United States Patent [19]
Wiedner et al.

[11] Patent Number: 5,538,012
[45] Date of Patent: Jul. 23, 1996

[54] SURGICAL DRAPING SYSTEM HAVING A REUSABLE AND A DISPOSABLE COMPONENT

[75] Inventors: Guenther Wiedner, Seeshaupt, Germany; John A. Duncan, Glenrothes; Suresh R. Patel, Dalgety Bay, both of Scotland

[73] Assignee: Rotecno AG, Zurich, Switzerland

[21] Appl. No.: 222,252

[22] Filed: Mar. 3, 1994

[30] Foreign Application Priority Data

Apr. 2, 1993 [EP] European Pat. Off. .............. 93105527
Jul. 19, 1993 [DE] Germany .......................... 43 24 136.0

[51] Int. Cl.$^6$ ..................................... A61B 19/08
[52] U.S. Cl. ..................... 128/853; 128/854; 128/849
[58] Field of Search ..................... 128/849–856

[56] References Cited

U.S. PATENT DOCUMENTS

| | | | |
|---|---|---|---|
| Re. 33,727 | 2/1991 | Sims ..................... | 128/851 |
| 3,060,932 | 10/1962 | Pereny et al. ............. | 128/849 |
| 3,561,439 | 2/1971 | Bayer ..................... | 128/853 |
| 3,721,234 | 3/1973 | Hadtke et al. ............ | 128/853 |
| 3,826,253 | 7/1974 | Larsh et al. .............. | 128/854 |
| 3,882,859 | 5/1975 | Ericson ................... | 128/854 |
| 3,916,887 | 11/1975 | Kelly ..................... | 128/851 |
| 4,024,862 | 5/1977 | Collins . | |
| 4,316,455 | 2/1982 | Stoneback ............... | 128/853 |
| 4,316,456 | 2/1982 | Stoneback ............... | 128/853 |
| 5,038,798 | 8/1991 | Dowdy . | |
| 5,078,154 | 1/1992 | Patel et al. .............. | 128/849 |

FOREIGN PATENT DOCUMENTS

| | | |
|---|---|---|
| 0185002 | 6/1986 | European Pat. Off. . |
| 0436852 | 7/1991 | European Pat. Off. . |
| 0507760 | 10/1992 | European Pat. Off. . |
| 1386800 | 3/1975 | United Kingdom . |
| 2018597 | 10/1979 | United Kingdom . |

*Primary Examiner*—Jessica J. Harrison
*Assistant Examiner*—Michael O'Neill
*Attorney, Agent, or Firm*—Townsend and Townsend and Crew

[57] ABSTRACT

A two-part surgical draping system comprising a disposable drape (1) for adhesion to an operation site, and one or more reusable drapes (6) placed over the disposable drape (1). The disposable drape (1) comprises a window (2), an upper absorbent layer (5) and a lower impermeable layer, first adhesive means (3) for adhering the lower impermeable layer to the patient, and non-adhesive preferably oppositely disposed margins (7) which serve to facilitate handling of the disposable drape (1). For attachment of the one or more reusable drapes (6) to the disposable drape (1), either the upper or the lower surface of the disposable drape is provided with second adhesive means (4) which is adherable to the lower or upper side of the reusable drape respectively. After attachment, the one or more reusable drapes (6) leave an access opening to the operation site. Moreover, the adhesive means (3,4) are preferentially protected prior to use by respective removable coverings (3',4').

18 Claims, 5 Drawing Sheets

SURGICAL DRAPING SYSTEM HAVING A REUSABLE AND A DISPOSABLE COMPONENT

BACKGROUND OF THE INVENTION

The present invention relates to a surgical draping system for retaining sterile and clean conditions at an operation site. Surgical drapes are well known in the medical community and serve to prevent contamination of the sterilized operation site by foreign bodies, in particular micro-organisms. Two important potential sources of infection of the patient are the transfer of bacteria originating from unsterilized areas of his own body to the exposed tissue at the operation site and the airborne transfer of bacteria from other sources to the operation site such as lint or skin particles originating from the surgeon or other staff in the operating theater.

In the prior art, a wide variety of draping systems have been employed to improve sterility at the site of an operation. It is helpful to consider the features of these diverse systems to gain an appreciation of the object and subject of the present invention.

There are two main classes of surgical drapes: reusable drapes and disposable drapes. Before considering the action of drapes, it should at first be appreciated that micro-organisms can only be transmitted in a medium. They do not move freely on their own, i.e. they are transferred by fluids, aerosol droplets, lint, dust particles, skin particles or the like.

Historically cotton drapes were and still are used, as they are absorbent and soak up liquids. However, they provide no bacterial barrier. Even when replaced by polyester cotton drapes treated with liquid repellent finish, the properties are limited and are lost after a few uses. Both cotton and polyester cotton drapes are lint producers from the beginning and this production increases with each use. Latter-day fabrics for reusable drapes, such as ROTECNO (registered trade mark), which similarly present a sterile barrier to prevent infection have improved properties in a number of respects. For instance the fabric is liquid repellent, thereby still functioning as a sterile barrier when contacted by liquids, non-particle generating, and provided with a grid of crossed conductive fibers to prevent the build-up of static electricity, which when present can attract airborne particles and on discharge damage sensitive electrical equipment.

In use, such drapes are arranged around the operation site and held in position with clips which grip through the fabric onto the flesh of the patient. A single drape may be used, in which case there is an aperture in the drape which is appropriately dimensioned to allow access to the operation site. If a plurality of drapes are used, these may have a simple rectangular shape and are laid over the patient and overlap each other to form, for instance, a rectangular access area around the operation site. However, with such draping systems it is difficult to efficiently seal off the operation site from the surrounding non-sterile regions of the patient, as openings remain between the patient's skin and the drape through which micro-organisms can be freely carried. One particularly undesirable mode of patient self-infection is when fluids spilled during the operation flow under or through the drape to non-sterile regions of the patient, become contaminated and then return to the operation site, for instance by capillary action or under the application of pressure.

These fabric drapes do possess the key advantage that they are reusable, the fabric construction being suitable for typical hospital cleansing methods such as laundering followed by steam sterilization. However, over a period of time, the clipped regions of the fabric become damaged, thereby leading to further degradation of the operational conditions.

To avoid some of the shortcomings of clipping drapes, adhesive tapes can be applied to the edges of the drapes to adhere them to the patient's skin.

After laundering the reusable drapes, double-sided adhesive tape, which has a backing paper, for instance siliconized paper, is attached to the edge of the drape. The reusable drape together with the tape now one-sidely adhered to it, is then sterilized, usually steam sterilized at, for instance, 134° C. Prior to the operation, the backing paper is pulled off the adhesive tape and the drape is adhered to the patient's skin at the site of the operation.

The problem then exists of thoroughly removing the adhesive tape from the drape. Experience has shown that it is tiresome to perform this manually, and therefore correspondingly difficult to supervise that overworked staff carry out this task adequately. In any case, residual traces of adhesive remain on the drape which must be fully removed by the cleansing or laundering procedure. This presents a particular complication for the adhesive, since it must satisfy conflicting requirements. Namely, on the one hand it must be able to withstand sterilization, in particular steam sterilization at 140° C., without losing its adhesive properties, and on the other hand it should be fully removable in the cleansing process, in particular in normal hospital laundering.

Certain acrylate adhesive tapes go some way to fulfilling this task. However, during cleansing, the dissolvable glue bleaches out the color from the textile reusable drape. This results in a reusable drape which is still completely serviceable giving the appearance of being old and worn, which, in turn, frequently leads to staff disposing of the drape prematurely. Substantial unnecessary costs are thereby incurred. Also, the use of such adhesive tape represents a very substantial cost factor. It has been found in practice that the operating theater actually spends substantially more money on tape provided with this special adhesive than on the reusable drapes to which it is adhered.

As an alternative method, disposable drapes are also used; they are typically comprised of a non-woven cellulosic material. In some versions, the central part of the disposable drape is adhered to the operation site, and such drapes can be provided with an absorbent upper surface which is reinforced with plastic under the absorbent layer to act as a bacterial barrier.

Although the best of these drapes may provide an acceptable bacterial barrier, drapes of this kind are not intended to be cleaned or reused. Given the high throughput achieved in a modern operating theater, the use of such disposable drapes leads to the creation of large amounts of waste material requiring incineration with the ensuing undesirable costs and environmental consequences.

Therefore, it can be seen that a large number of approaches have been used in prior art draping arrangements and systems, each individual approach offering certain advantages but always associated with certain other disadvantages.

One general problem for all draping systems is that the number and variety of special drape designs required to meet all types of operations results in considerable costs, large storage space utilization and great administrative effort required to efficiently maintain adequate stocks of these items ready for operations.

SUMMARY OF THE INVENTION

It is an object of the present invention to provide a draping system which provides a high standard of sterility at favorable cost, is convenient to use, avoids the previous problems encountered with the use of adhesive tape and avoids the production of large amounts of waste material.

To satisfy this object, the present invention provides a surgical draping system, comprising a disposable element for adhesion at its lowest surface using first adhesive means to the operation site and a reusable drape or reusable drapes disposed about said disposable element and defining an opening providing access to the operation site through the disposable element, and is characterized in that the disposable element is itself formed as a disposable drape having a window therein and a lower impermeable layer and an upper absorbent layer, defining an absorbent surface; in that this disposable drape is provided for adhesion to said reusable drape or drapes; and in that said reusable drape or drapes leave an opening exposing at least part of the absorbent surface and the window.

In one basic and preferred variant, the disposable drape is provided on its upper surface with second adhesive means surrounding the absorbent surface for adhesion to the lower side of the reusable drape or drapes.

Alternatively, in a second variant, the disposable drape can be provided on its lower surface with second adhesive means surrounding the first adhesive means for adhesion to the upper side of the reusable drape or drapes.

This solution is partly based on the recognition that the incision foil can be used additionally to secure the reusable drape which is in any case required. This subtle solution enables virtually all the positive features present in the various prior art draping systems to be combined in a single draping system.

The absorbent upper surface of the disposable drape is provided in order to wick or soak up fluids arising from the operation, whereas the lower layer of the disposable drape advantageously constitutes a barrier to the passage of liquids and micro-organisms therethrough.

Moreover the adhesive bond to the reusable drape or drapes prevents the transfer of infection from the non-sterilized areas of the patient to the surgical wound. When removing the reusable drape or drapes, they are automatically separated from the disposable drape so that no adhesive remains on them. This arrangement also has the very substantial benefit that the adhesive no longer has to satisfy the conflicting requirements of being fully removable at the cleansing stage while possessing adhesive properties which are unaffected by both sterilization or by becoming wet during the operation. This is achieved simply because there is no longer any adhesive on the reusable drape during laundering and sterilization of the reusable drape. Additionally, costly adhesives no longer have to be used which discolor the drape.

The disposable drape is now made in relatively small sizes, being only slightly larger than the opening in the corresponding reusable drape so that the volume of waste material produced is minimized.

For practical reasons, it is also advantageous to contrive the second adhesive means in such a way that it bonds substantially more weakly to the reusable drape than the first adhesive means bonds to the patient. This ensures that on removal of the drape, after completion of the operation, the disposable drape initially remains on the patient, preventing any tendency which overworked or tired staff may have to throw away the reusable drape together with the disposable drape.

Additionally, the second adhesive means of the disposable drape is preferentially contrived in such a way that it bonds substantially more weakly to the reusable drape or drapes than to the disposable drape. This ensures that when the reusable drape is separated from the disposable drape, the second adhesive means remains on the disposable drape and also avoids that the disposable drape goes to the laundry with the reusable drape or drapes.

The window provided in the disposable drape may be formed as an aperture in the disposable drape, thereby defining an open window, or may be covered, for instance with transparent plastic, in which case it should be readily removable or rupturable, in particular incisable, to provide access to the operation site when required.

The disposable drape, which is typically supplied in a sterile pack, will advantageously possess further qualities, such as for instance that the first and second adhesive means are protected prior to their respective use by appropriate removable siliconized coverings, for instance siliconized paper coverings, and that it is provided with at least substantially oppositely disposed peripheral flaps which are free from adhesive means and facilitate the deployment and removal of the disposable drape, as they may be conveniently gripped, in particular by hand.

In the first variant of the current invention, a reusable drape for use in a draping system of the kind provided above may be beneficially provided with an opening matched in shape to the absorbent surface of the disposable drape for which it is intended and have a marginal region surrounding the opening in the reusable drape for adhesion to the disposable drape by adhesive means provided on the disposable drape. An analogous provision can be made in the second variant of the current invention, where, in this case, the opening is matched in shape to the first adhesive means instead of to the absorbent surface due to the marginal region of the reusable drape being adhered to the lower side of the disposable drape instead of to the lower side.

The reusable drape is beneficially made of non-wicking and/or non-absorbent material. An advantage of such liquid repellent, in particular hydrophobic, materials lies in the integrity of the sterile barrier which they provide even when covered in liquid. This liquid repellency keeps soiling of the reusable drape to a minimum and ensures that the patient remains unsoiled. Any slight spillages of fluid during the operation will in any case be taken up by the upper absorbent surface layer of the disposable drape. In particular, the reusable drape can be made of a single layer material which forms a barrier to liquids and/or micro-organisms. Diathermy and suction tubes can be attached to the reusable drape using non-penetrating ball and socket clips.

It is intended, and also feasible, to clean, especially launder, and sterilize, in particular steam-sterilize, the reusable drape and to make the reusable drape from material with non-particle generating and/or antistatic properties.

The reusable drape can be fashioned from a single piece of fabric provided with a rectangular aperture which is slightly smaller than the outer dimensions of a disposable drape with which it is designed to be used. The aperture is so dimensioned that its rim has the same shape as the inner edge of the disposable drape's second adhesive means, so that the reusable drape can be adhered onto the disposable drape. In both variants, the reusable drape does not encroach upon the region of absorbent material in order that access to the operation site is as free as possible. Moreover, the potential for soiling the reusable drape is minimized.

By standardizing the outer dimensions of the disposable element it is possible to use one type of reusable drape for different types of operation.

Another alternative scheme offering advantages of an organizational kind is to use several reusable drapes in a given draping arrangement, wherein the reusable drapes are connectable to a portion of the second adhesive means, and wherein a sufficient number and variety of shapes of these pieces are provided to establish a similarly comprehensive and effective region of protection as that provided by the above single reusable drape draping arrangement.

In a given operating theater or hospital, one may envisage a number of differently sized and/or shaped disposable drapes being held in stock for use in different operations, and it can therefore be appreciated that in the previously described case where only one reusable drape is used in a given draping arrangement, one size of reusable drape must be held in stock for every one size of disposable drape. Through the use of multiple piece drapes, there is the possibility of reducing the number of reusable drapes required by adopting a modular approach. In a simple implementation, where the peripheries of the disposable drapes are always rectangular, only two different types of reusable drapes would be required; namely corner types and edge types. Such a modular approach would therefore offer substantial organizational and inventorial benefits in the day-to-day running of the hospital and its operating theaters.

To summarize, the physically largest part of the draping system of the invention, namely the reusable drape, can be used many times, without either expensive high performance adhesive means or clipped attachment to the patient. The Hobson's choice of the prior art between either providing a good seal to prevent patient self-infection or having ease of reuse of the drape has thereby been removed.

Furthermore, as a result of the longevity of the reusable drape, it can be made of modern, relatively expensive, material, the performance of which is superior in many departments over any material cheap enough to be suitable for such a large disposable item.

The disposable part is relatively small and so the amount of waste generated by the draping system of the invention is kept to a low level. In any case, the item immediately surrounding the operation site will be the most heavily soiled, and thus it is favorable that the item covering this area be disposable and of as small a size as practicable, as is provided by the present invention.

DETAILED DESCRIPTION OF THE PREFERRED EMBODIMENTS

Figure 1A:
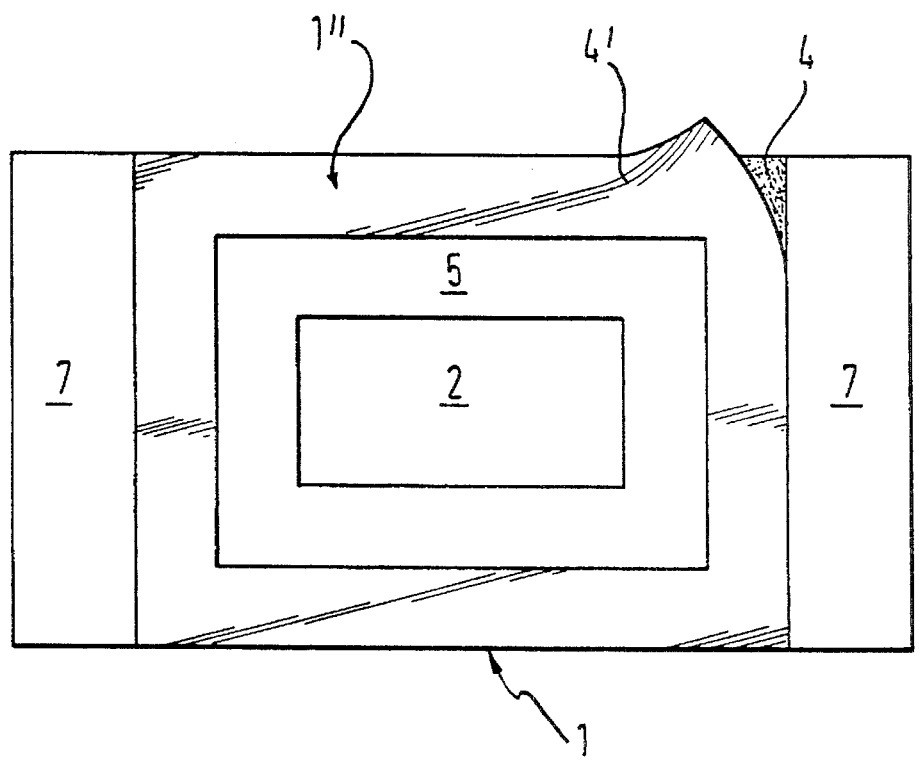
FIGS. 1A and B show a disposable drape of a first embodiment, as seen from above and below, respectively, FIGS. 2A and B show a disposable "U" drape with an opening on one side according to a second embodiment, as seen from above and below, respectively.
Figure 1B:
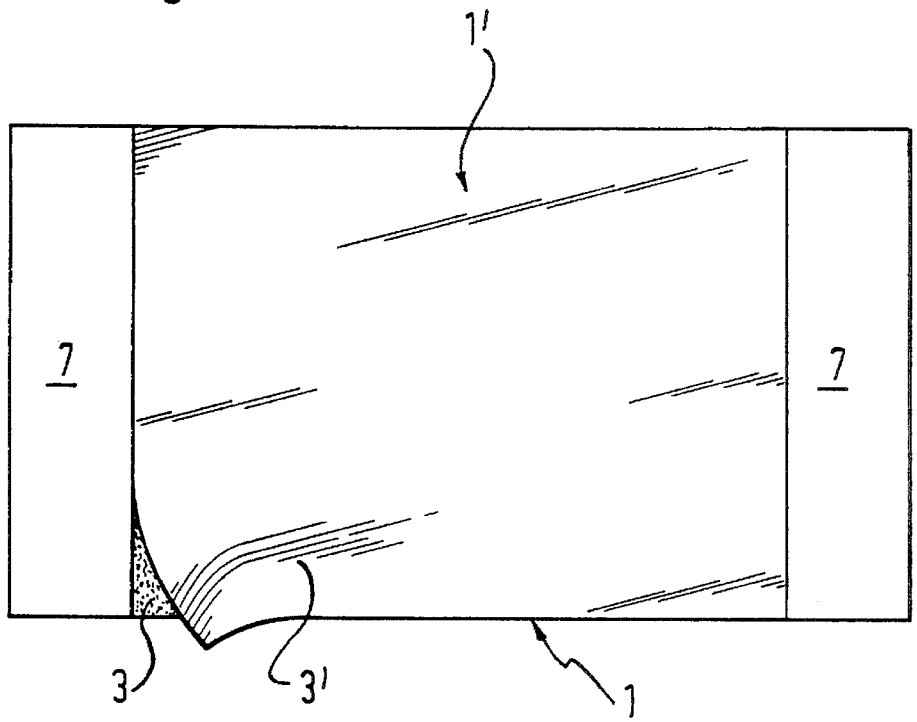

A disposable drape 1 according to a first embodiment of the draping arrangement is shown in FIG. 1.

Here, the disposable drape 1 is built up on a transparent rectangular plastic sheet or foil, the central area of which will form the window 2 through which the operation site is to be accessed and the periphery of which will define the periphery of the disposable drape 1. With the exception of two peripheral flap regions 7, the whole of the bottom side 1' of the plastic sheet is coated with adhesive to form the first adhesive means 3. The first adhesive means is then protected prior to use by a siliconized paper cover 3' which is to be peeled off at the appropriate time. Reference numeral 3' in fact points to a corner of the cover which is in the process of being peeled off.

A second adhesive coating is provided on the other, i.e. top, side 1" of the plastic sheet, to form the second adhesive means 4, wherein the siliconized paper cover 4' on the side facing away from the plastic sheet is likewise retained until use. A piece of absorbent material 5, having a central hole which defines the window 2 and outer dimensions which are sufficiently small to enable it to fit within the strips of double-sided adhesive tape comprising the second adhesive means 4, is provided on the top side 1" of the plastic sheet.

As briefly mentioned above, oppositely disposed regions are left free of adhesive on the periphery of the plastic sheet, thereby forming flaps 7 which are large enough to be taken hold of, in particular by hand, to aid the application and removal of the disposable drape. A thus constructed complete disposable drape may be sterilized and stored in a sterile package until use.

It will be appreciated that the adhesive layers may be provided in several ways, for instance by spraying or transfer rolling a film of adhesive onto the plastic sheet, by using double-sided adhesive tape. The exposed adhesive surface of this adhesive layer is then protectable by a peel-off cover.

Also, it is not necessary that the base sheet of the disposable drape be of a unitary plastic construction. One could for instance envisage substituting the hitherto described plastic sheet by a fibrous, for instance paper, or woven, for instance liquid repellent, sheet having a centrally arranged plastic window. Alternatively, the window 2 may be an open window 2, that is an access hole or cut-out which is always present in the disposable drape.

Figure 2A:
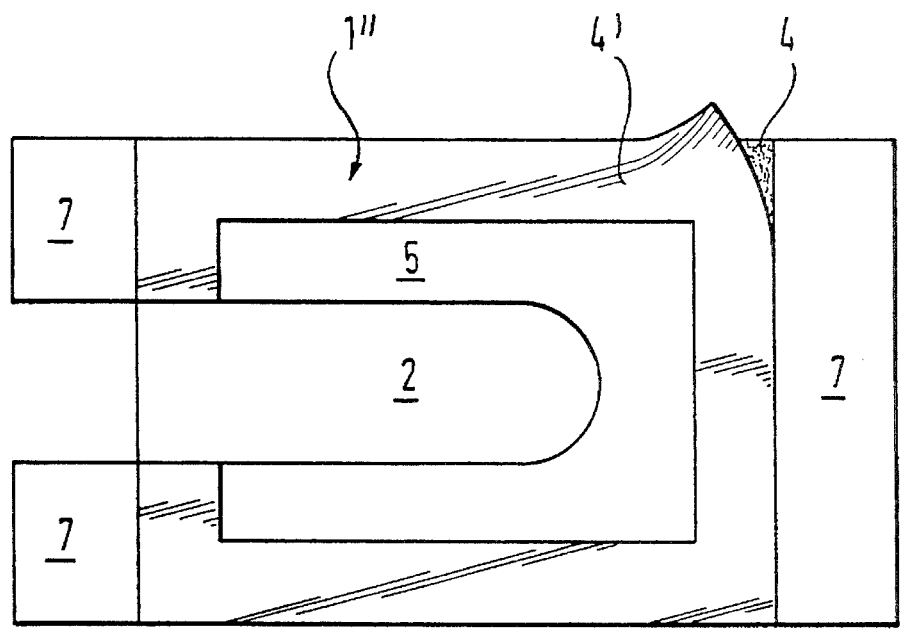
Figure 2B:
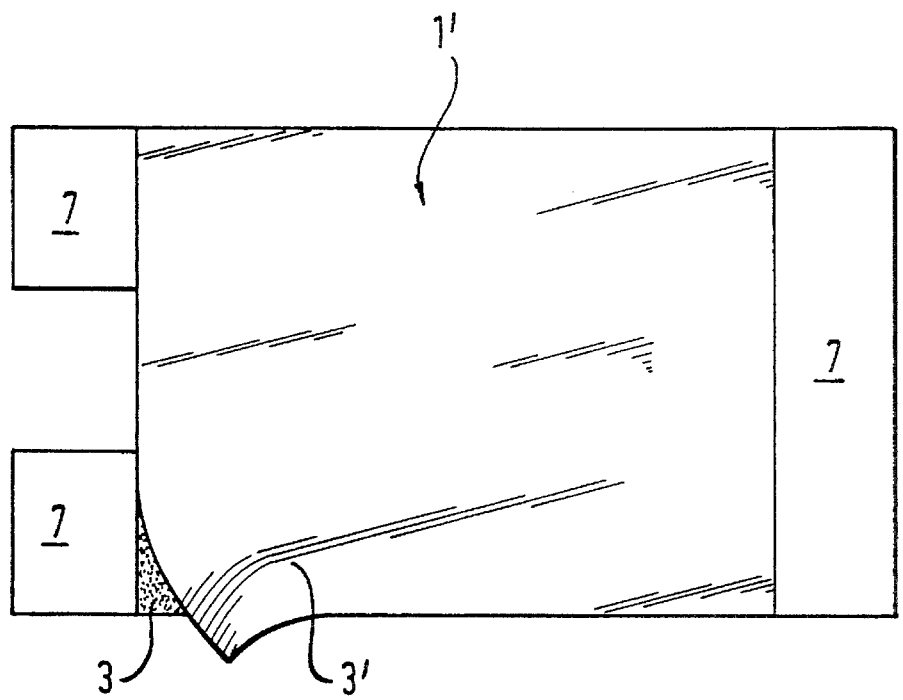

The disposable element can also be produced in other shapes, such as in the split-U shape in accordance with a second embodiment of the disposable drape shown in FIGS. 2A and 2B, and used for example to fit various extremities of the patient's body. The reference numerals used in FIGS. 1A and 1B have also been used in FIGS. 2A and 2B, and it will be understood that the same reference numerals designate parts having the same design and/or function so that the description in connection with FIGS. 1A and 1B also applies in the same sense to FIGS. 2A and 2B.

A reusable drape 6 is now described, which, together with a disposable drape 1, forms a draping arrangement (see FIG. 3) according to a first embodiment of the invention.

The reusable drape 6 is made out of a piece of material having an aperture which is slightly smaller than the outer dimensions of a given type of disposable drape 1 with which it is designed to be used. More specifically, the aperture is so dimensioned that its rim has the same shape as the inner edge of the disposable drape's second adhesive means (4), so that the reusable drape 6 can be adhered onto the disposable drape 1 by the second adhesive means 4. Additionally, when used in conjunction with the above described disposable drape 1 of this embodiment, the reusable drape 6 should encroach very little, or not at all, upon the region of absorbent material 5 in order that access to the operation site remains as free as possible and that the potential for soiling the reusable drape 6 during the operation is kept to a minimum.

In a modification, several reusable drapes 6 are used in conjunction with the disposable drape of for instance the first embodiment to form the draping arrangement. When these reusable drapes 6 are suitably combined, they provide similar coverage to that provided by the reusable drape 6 of the first embodiment. The advantage of incorporating a multiplicity of reusable drapes 6 in a given draping arrangement lies in that a draping system can be developed wherein one and the same shape and size of reusable drape 6 can be used to form draping arrangements for variously shaped and sized disposable drapes 1, a stock of the latter being necessary for performing different operations.

Deployment of the disposable drape (1) and reusable drape (6) of the first embodiment of the draping arrangement may be performed as follows.

Figure 3:
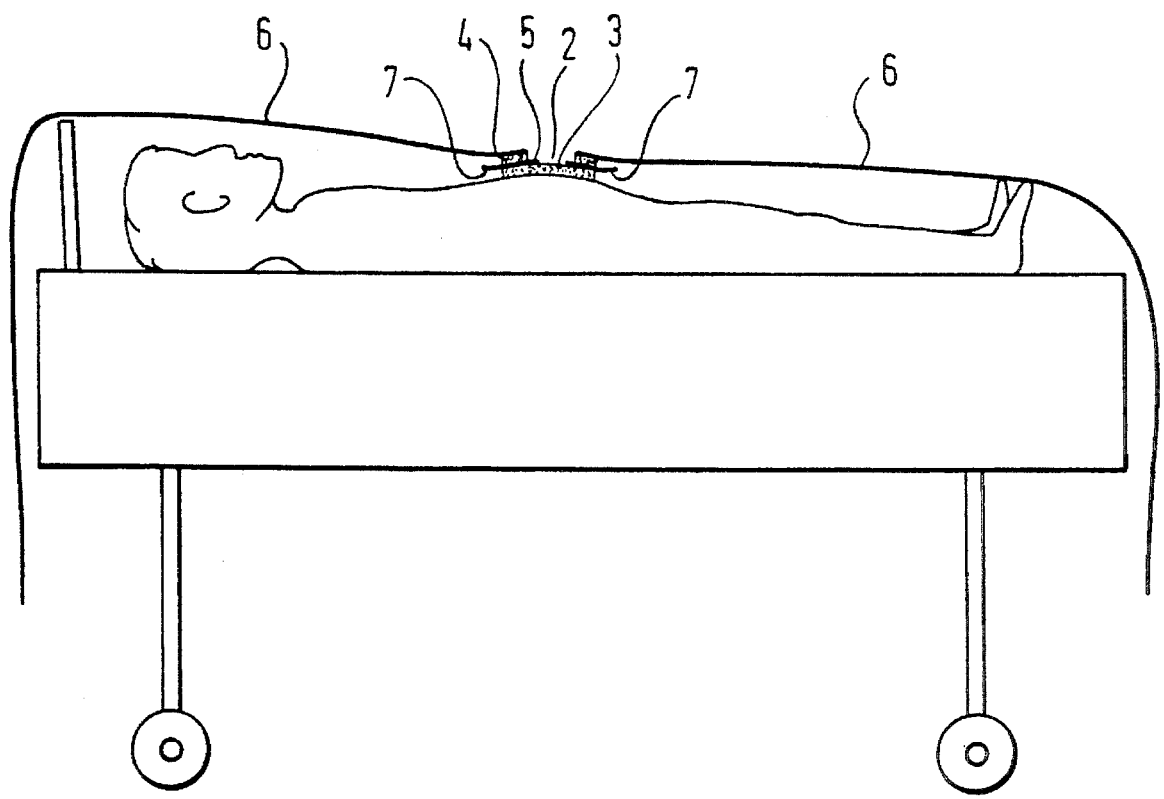
FIG. 3 is a cross-section of a draping arrangement according to the first embodiment using the disposable drape of FIG. 1 together with a reusable drape, FIGS. 4A and B show a disposable drape of a third embodiment, as seen from above and below, respectively.

The operation site is sterilized. One member of the staff removes the disposable drape from its packaging and holds it taut by its peripheral flaps 7, while another staff member removes the siliconized paper covering 3' from the first adhesive means 3. The disposable drape 1 now being positioned so that the window 2 is central over the operation site, the disposable drape 1 is then stuck down. The siliconized paper covering 4' is then removed from the second adhesive means 4. The reusable drape or drapes 6 is/are now positioned over the disposable drape 1, so that the periphery of the hole in the former lies adjacently over the inner periphery of the second adhesive means 4 of the latter, and is then stuck down. For the time being, the window 2 remains complete and thus protects the sterilized operation site from airborne contamination. Subsequently, the window 2 is cut through by the surgeon, typically with a scalpel, directly before the commencement of invasive surgery. The situation pertaining during the operation is depicted in FIG. 3.

Figure 4A:
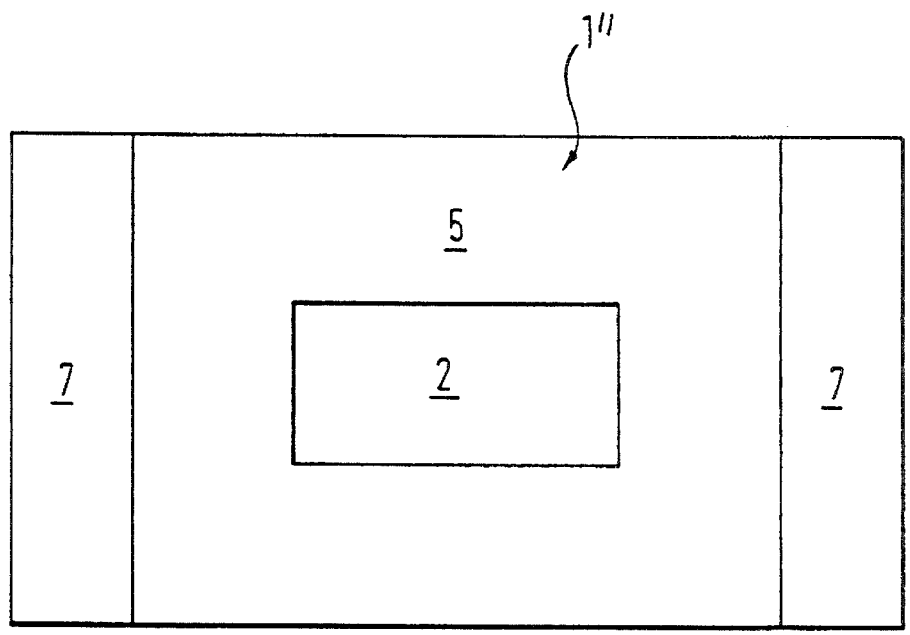
Figure 4B:
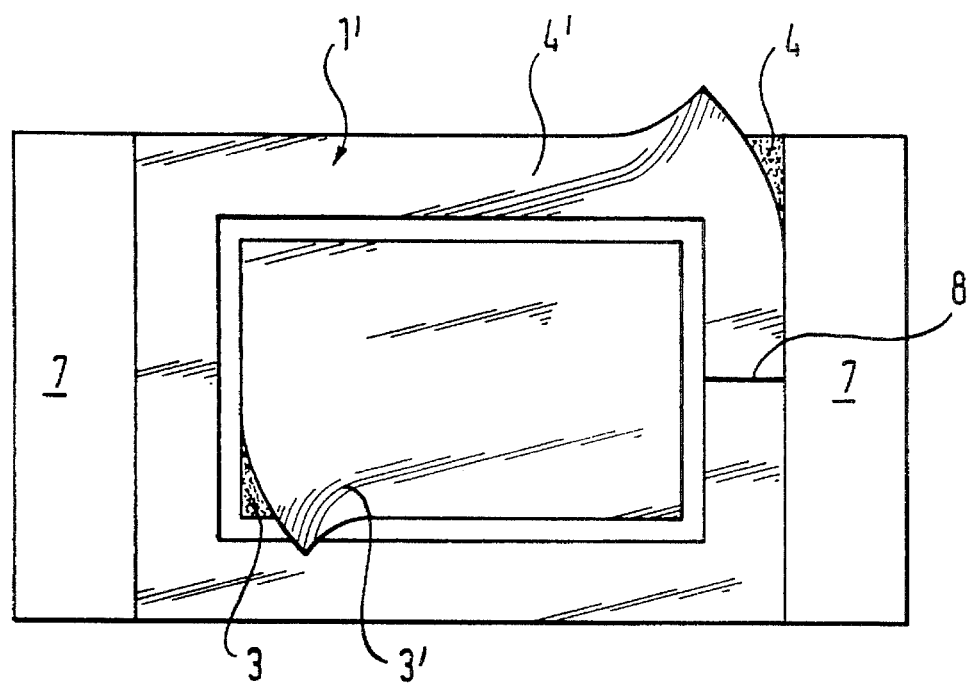

A disposable drape 1 according to a third embodiment is shown in FIGS. 4A and 4B. As in the first and second embodiments, the disposable drape 1 is constructed starting from a transparent rectangular plastic sheet or foil. A central portion of the bottom side 1' of the plastic sheet is coated with adhesive to form the first adhesive means 3. The first adhesive means is protected prior to use by a siliconized paper cover 3' which is to be peeled off at the appropriate time. Reference numeral 3' in fact points to a corner of the cover which is in the process of being peeled off.

In contrast to the first and second embodiments, in the third embodiment the second adhesive means is provided on the bottom side 1' of the plastic sheet, i.e. on the same side as the first adhesive means 3. The second adhesive means 4 is disposed outside the periphery of the first adhesive means 3 and, as before, the respective siliconized paper cover 4' is retained until use.

As becomes clear below in the passage describing a method of deployment of the draping arrangement, it is advantageous in this embodiment if the siliconized paper cover 4' is not a single continuous piece, because if it were it would have hoop-like shape and could be inconvenient to peel off. A single break or cut 8 can be provided in the "hoop" as is shown in FIG. 4B. Alternatively more breaks could be provided, in which case the cover 4' would comprise more than one piece. The above feature facilitates removal of the siliconized paper cover 4' when it is not removed until after the first adhesive means 3 has been stuck down on the patient.

On the upper side 1" of the plastic sheet, an absorbent surface 5 is provided, which has a central aperture defining the window 2. Since the second adhesive means is on the bottom side 1' in this embodiment, the area available for the absorbent surface 5 on the top side 1" is, all things being equal, correspondingly larger. Flaps 7 are also provided which serve the same purpose as those provided in the first embodiment. Also the various constructive modifications and alternatives concerning, for instance, the provision of the adhesive means, the base sheet and the window detailed above for the first embodiment are equally valid for the third embodiment.

Furthermore, a fourth embodiment could be envisaged having the split U-shape of the second embodiment and the second adhesive means 4 arranged on the lower side 1' in an analogous fashion to the third embodiment.

Deployment of the disposable drape 1 of the third embodiment in conjunction with a one piece surgical drape 6 is performed along broadly similar lines to the deployment described above for the first embodiment. The operation site is sterilized. One member of the staff removes the disposable drape from its packaging and holds it taut by its peripheral flaps 7, while another member of the staff removes the siliconized paper covering 3' from the first adhesive means 3. The disposable drape 1 is then taken over to the patient and positioned so that the window 2 is centered over the operation site. The disposable drape 1 is then stuck down.

At this stage the method of deployment differs somewhat from that described for the first embodiment. Namely, the edge of the aperture in the reusable drape 6 is tucked under the periphery of the disposable drape, so that the edge of the aperture in the reusable drape lies adjacent to but beneath the inner periphery of the second adhesive means 4 of the disposable drape. Only then is the siliconized paper covering 4' removed from the second adhesive-means 4 and the latter stuck to the surgical drape 6.

It is for this reason that it is advantageous when the siliconized paper covering 4' is not a single continuous piece, because if it were it would have hoop-like shape and could be inconvenient to peel off. One could, for instance provide at least one break in the "hoop", or form the cover 4' from more than one piece.

Figure 5:
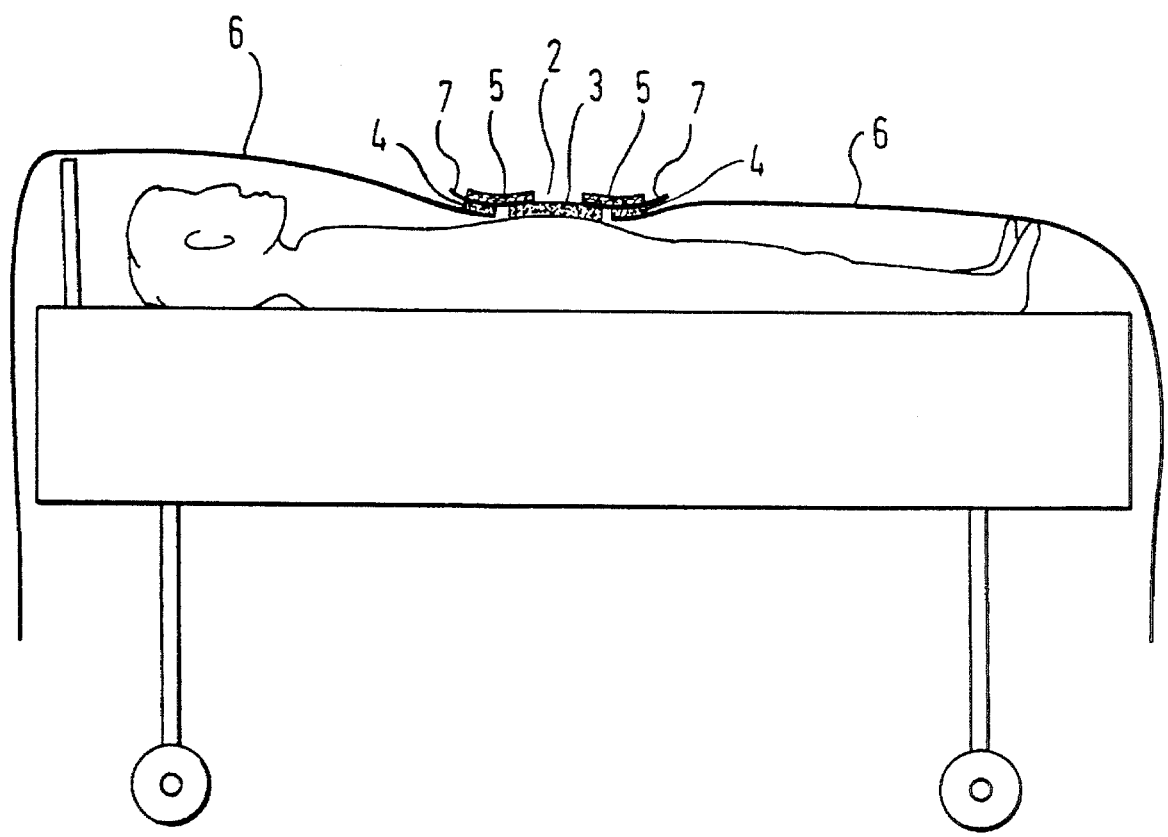
FIG. 5 is a cross-section of a draping arrangement according to a third embodiment of the invention using the disposable drape of FIG. 4 together with a reusable drape.

Then, as for the first embodiment, the window 2 is left complete, an access hole subsequently being cut in it only directly before the commencement of invasive surgery. The situation pertaining is shown in FIG. 5.

For the sake of completeness it is pointed out that the reusable drapes used for the purposes of the present invention can be designed in the same manner as existing reusable drapes and are available from the company Rotecno AG, Steinstrasse 35, 8045 Zürich, Switzerland. The disposable drapes can be basically similar to those available from the 3M or Kimberly-Clark companies, for example, but require the addition of the second adhesive means and the use of sizes matched to the reusable drapes so as to adapt the disposable drapes for use in the draping system of the present application.

For the sake of emphasis it is pointed out that when realizing the disposable drape as a sheet of plastic the window therein may be formed as a closed window, in which case the transparent or translucent plastic sheet does not have an opening therein but itself defines the window. In this case the surgeon then cuts the plastic away at the site of the surgical incision to obtain access to the patient. Alternatively the window can be an open window, that is to say an opening in the sheet of plastic through which the surgeon automatically has access to the site of the operation. If the disposable drape is made of another material which is not sufficiently transparent or translucent then the window provided therein can be formed by a transparent or translucent plastic sheet or can also be an open window.

We claim:

1. A surgical draping system comprising:
   a) a disposable impermeable drape having a lower surface and an upper surface, first adhesive means at said lower surface for adhesion to an operation site on a patient, a window, an absorbent layer surrounding said window and second adhesive means at said lower surface surrounding said first adhesive means; and
   b) at least one reusable drape having an opening therein and placeable in use under said disposable drape so that said opening surrounds said first adhesive means, said second adhesive means having a first bond strength to said at least one reusable drape and a second bond strength to said disposable drape with said first bond strength being substantially lower than said second bond strength, whereby, on separation of said at least one reusable drape from said disposable drape, substantially all said second adhesive means remains on said disposable drape.

2. A surgical draping system in accordance with claim 1, wherein said first adhesive means has a bond strength to said patient substantially greater than said first bond strength, whereby, on removal of said at least one reusable drape, said disposable drape initially remains on said patient.

3. A reusable drape in accordance with claim 1, wherein said reusable drape is made of non-absorbent material.

4. A reusable drape in accordance with claim 1, wherein said reusable drape does not generate particles.

5. A reusable drape in accordance with claim 1, wherein said reusable drape has antistatic properties.

6. A surgical draping system in accordance with claim 1, wherein said second adhesive means forms a closed loop surrounding said first adhesive means.

7. A surgical draping system in accordance with claim 1, wherein said disposable drape has a lower impermeable layer forming a barrier to the passage of liquids and micro-organisms therethrough.

8. A surgical draping system in accordance with claim 1, wherein said window of said disposable drape is one of removable and rupturable to provide access to said operation site.

9. A surgical draping system in accordance with claim 1, wherein said window is formed by an aperture in said disposable drape.

10. A surgical draping system in accordance with claim 1, including a removable covering for protecting said first adhesive means prior to use.

11. A surgical draping system in accordance with claim 1, including a removable covering for protecting said second adhesive means prior to use.

12. A surgical draping system in accordance with claim 11, wherein said removable covering comprises siliconized paper.

13. A surgical draping system in accordance with claim 1, including a sterile pack housing said disposable drape.

14. A surgical draping system in accordance with claim 1, wherein said disposable drape is provided with at least substantially oppositely disposed handling margins which are free from adhesive means.

15. A reusable drape for use in a surgical draping system including a disposable drape having a lower surface and an upper surface, first adhesive means at said lower surface for adhesion to an operation site on a patient, a window, an absorbent layer surrounding said window and second adhesive means at said lower surface surrounding said first adhesive means, the reusable drape comprising an opening therein and being placeable in use under said disposable drape so that said opening surrounds said first adhesive means, said second adhesive means having a first bond strength to said at least one reusable drape and a second bond strength to said disposable drape with said first bond strength being substantially lower than said second bond strength, whereby, on separation of said at least one reusable drape from said disposable drape, substantially all said second adhesive means remains on said disposable drape, the opening being matched in shape to an outer boundary of said first adhesive means of said disposable drape and a marginal region surrounding said opening, for adhesion to said disposable drape by said second adhesive means.

16. A reusable drape in accordance with claim 15, wherein said reusable drape is made of non-wicking material.

17. A reusable drape in accordance with claim 15, wherein said reusable drape is made of a material which forms a barrier to liquids and micro-organisms.

18. A reusable drape in accordance with claim 15, wherein said reusable drape is launderable, and sterilizable.

* * * * *